United States Patent [19]

Berkman et al.

[11] 4,039,684

[45] Aug. 2, 1977

[54] METHOD FOR TREATMENT OF *CANINE SEBORRHEA*

[75] Inventors: Robert N. Berkman, Cranford; Jesse W. Houdeshell, Scotch Plains, both of N.J.

[73] Assignee: Schering Corporation, Kenilworth, N.J.

[21] Appl. No.: 670,337

[22] Filed: Mar. 25, 1976

[51] Int. Cl.² ............................................ A61K 31/165
[52] U.S. Cl. ............................................ 424/324
[58] Field of Search ........................................ 424/324

[56] References Cited

PUBLICATIONS

Chem. Abst. 8th Collect. Index, vol. 66–75, 1967–1971 p. 28085s.

*Primary Examiner*—Sam Rosen
*Attorney, Agent, or Firm*—Vincent H. Gifford; Bruce M. Eisen; Stephen B. Coan

[57] ABSTRACT

A method for the treatment of *Canine seborrhea* comprising oral administration of a daily dosage of 5–25 mg/kg of either 4-nitro-3-trifluoromethylisobutyranilide or its metabolite 4'-nitro-3'-trifluoromethyl-2-hydroxyisobutyranilide.

5 Claims, No Drawings

METHOD FOR TREATMENT OF CANINE SEBORRHEA

Canine seborrhea is a recognized chronic skin disorder of dogs which may affect the entire body surface or be restricted to certain areas. The disease, which often remains with a dog for life, is characterized by increased scale formation and abnormal sebum secretion, with follicular plugging, oiliness, loss of hair, pruritus, erythema and a rancid odor being common. This condition may worsen in the wintertime, with the affected skin rendered more susceptible to bacterial infections. The etiology of canine seborrhea is generally obscure.

This disorder has been extensively described in the literature, e.g. Muller and Kirk, SMALL ANIMAL DERMATOLOGY, 1969, Chapter 46; COMPENDIUM OF VETERINARY DERMATOLOGY, Pfizer Labs, 1959, p. 21–22; CANINE MEDICINE, First Catcott Edition, American Veterinary Publications, Inc., 1968, pp. 521–522, Kirk, R.W. seborrhea CURRENT VETERINARY THERAPY, III, 1968, p. 288, and Muller Canine seborrhea, ANIMAL HOSPITAL, 2:228–235, 1966.

Various treatments for Canine seborrhea are in use, such as frequent bathing or shampooing and the administration of corticosteroids or antibiotics. These treatments have, however, generally been unsatisfactory in that they oftentimes fail to treat all of the symptoms and generally provide only temporary relief.

We have found that effective, long lasting relief from the symptoms of Canine seborrhea can be obtained by oral administration to the afflicted dog of either 4-nitro-3-trifluoromethylisobutyranilide or its metabolite 4'-nitro-3'-trifluoromethyl-2-hydroxyisobutyranilide.

Both of these compounds have previously been reported to have antiandrogenic properties. See British Pat. No. 1,360,001 and South African Pat. No. 73/8858.

Generally, a single daily dose of 5–25 mg. per kg. of body weight of the above compounds will substantially relieve the condition in about 10 to 15 days and will usually return a dog to normal in about 30 days. A daily dosage regimen of approximately 10 mg. of active compound per kg. of body weight once a day is preferred.

A tablet is the preferred dosage form although it would be possible to orally administer the compound in other ways, e.g. mixing in powder or liquid form with food.

Various standard ingredients may optionally be included in the dosage form such as preservatives; lubricants, e.g. magnesium stearate; excipients (diluents), e.g. lactose; surfactants, e.g. sodium lauryl sulfate; binders, e.g. polyvinylpyrrolidone; disintigrants, e.g. corn starch.

The following nonlimiting example is presented to illustrate an orally administered tablet. All concentrations are by weight unless otherwisespecified.

| Ingredient | mg/Tablet |
| --- | --- |
| 4-nitro-3-trifluoromethylisobutyranilide | 100.0 |
| lactose, hydrous | 383.0 |
| sodium lauryl sulfate | 12.0 |
| polyvinylpyrrolidone | 25.0 |
| corn starch | 77.0 |
| magnesium stearate | 3.0 |
| | 600.0 |

The above tablet was orally administered once each day to a 7 year old female dachshund weighing about 7 kg. The animal was known to have suffered from a general seborrheic condition for at least six months. Prior to medication the animal had a rancid odor and showed signs of extreme oiliness, scaliness, dandruff, pruritus and hair loss. Following 15 days of treatment, the signs were greatly reduced and by 30 days the animal appeared to be normal. The animal remained normal through 90 days of medication.

Four of the above tablets were orally administered once a day to a 5 year old male german shepard weighing about 43 kg. The animal was known to have suffered from a general seborrheic condition for at least six months. Prior to medication the animal had a ancid odor and showed signs of extreme oiliness, scaliness, dandruff, pruritus, inflammation and hair loss. After 15 days of treatment, the signs were reduced and after 30 days of treatment the animal was nearly clinically normal.

Numerous other variants of the above composition will be apparent to one skilled in the art.

We claim:

1. A method of treating Canine seborrhea comprising the step of orally administering to a dog afflicted therewith an effective amount of a compound selected from the class consisting of 4-nitro-3-trifluoromethylisobutyranilide and 4'-nitro-3'trifluoromethyl 2-hydroxyisobutyranilide.

2. A method as in claim 1 wherein said oral dose is in the form of a tablet.

3. A method according to claim 1 werein said effective amount is within the range of 5 to 25 mg. per kg. of body weight.

4. A method according to claim 3 wherein said effective amount is approximately 10 mg. per kg. of body weight.

5. A method according to claim 1 wherein said compound is 4-nitro-3-trifluoromethylisobutyranalide.

* * * * *